United States Patent [19]

Yoneda et al.

[11] 4,272,517

[45] Jun. 9, 1981

[54] PERMANENT WAVING COMPOSITIONS

[75] Inventors: Koji Yoneda, Amagasaki; Takehisa Ohashi, Kobe; Masami Onishi, Akashi; Hirotaka Fukumitsu, Kakogawa, all of Japan

[73] Assignee: Kanegafuchi Kagaku Kogyo Kabushiki Kaisha, Osaka, Japan

[21] Appl. No.: 40,969

[22] Filed: May 21, 1979

[30] Foreign Application Priority Data

Dec. 25, 1978 [JP] Japan ................................. 53/164712

[51] Int. Cl.³ ............................................. A61K 7/09
[52] U.S. Cl. ...................................... 424/72; 424/319
[58] Field of Search ...................... 424/319, 71, 72, 70

[56] References Cited

U.S. PATENT DOCUMENTS

| | | | |
|---|---|---|---|
| 2,841,530 | 7/1958 | Andersen et al. | 424/71 X |
| 3,242,052 | 3/1966 | Sheffner | 424/72 X |
| 4,139,610 | 2/1979 | Miyazaki et al. | 424/71 |
| 4,153,681 | 5/1979 | Shiba | 424/71 |

FOREIGN PATENT DOCUMENTS

| | | | |
|---|---|---|---|
| 2658424 | 2/1978 | Fed. Rep. of Germany | 424/72 |
| 4858150 | 8/1973 | Japan | 424/72 |

*Primary Examiner*—Dale R. Ore
*Attorney, Agent, or Firm*—Armstrong, Nikaido, Marmelstein & Kubovcik

[57] ABSTRACT

A permanent waving composition which comprises N-carbamoylcysteine and which acts mildly on the human hair and skin and has outstanding stability during application and storage. When further incorporating cysteine, the composition posseses the advantages afforded by cysteine without involving the drawbacks attendant on the use of cysteine.

7 Claims, No Drawings

PERMANENT WAVING COMPOSITIONS

BACKGROUND OF THE INVENTION

Permanent waving compositions heretofore most extensively used consist predominantly of thioglycolic acid which has a peculiar unpleasant odor. It is also known that thioglycolic acid acts intensively on the human hair, that it is therefore liable to break or remove the hair or reduce the luster of the hair, and that causes a rash on the scalp or damage to the skin and to hair roots. In recent years, cysteine which has no unpleasant odor and acts moderately on the hair and skin has been introduced into considerably wide use as the main ingredient of permanent waving compositions in place of thioglycolic acid having the above drawbacks. Permanent waving compositions consisting mainly of cysteine, nevertheless, are prone to deteriorate during preservation owing to the oxidation of cysteine to cystine which is hardly soluble in water and separates out as crystals to seriously reduce the commercial value of the compositions. During permanent waving, cystine is also likely to separate out in the form of crystals as deposited on the hair or scalp of the customer or on the hands of the hair-dresser, consequently giving a disagreeable feeling. Since crystals of cystine are not removable even when washed with water, the deposition of cystine leads to a reduced work efficiency, possibly leaving white powder on the hair to impart an unattractive appearance to the finished hair. Moreover, cystine, when adhering to the hands of the hair-dresser, especially to crotches of her fingers, becomes firmly bonded to the skin and is not easily removable. Presently this poses an occupational problem pertaining to the hair-dressers.

Attempts have been made to remedy the foregoing drawbacks of permanent waving compositions comprising cysteine as the main ingredient. Published Examined Japanese Patent Application No. 14934/1973, for example, discloses addition of thioglycolic acid to provide a waving composition having improved storage stability. However, thioglycolic acid, which has a peculiar unpleasant odor and acts intensively on the hair and skin as mentioned above, deteriorates the advantages of the composition afforded by cysteine which has a mild action and no objectionable odor. Thus the use of thioglycolic acid should preferably be avoided. Published Unexamined Japanese Patent Application No. 128241/1977 proposes conjoint use of cysteine and N-acetylcysteine to give enhanced stability to the composition during application. The proposal nevertheless has the drawback that sufficient stability, if achievable, requires the use of a relatively large quantity of N-acetylcysteine which is expensive.

SUMMARY OF THE INVENTION

The present invention relates to novel permanent waving compositions comprising N-carbamoylcysteine. The invention contemplates provision of permanent waving compositions which act mildly on the human hair and skin, are free from any unpleasant odor and have outstanding stability during storage and application.

Typically this invention provides permanent waving compositions comprising 3 to 20% by weight of N-carbamoylcysteine as a main ingredient and in the form of an aqueous solution having a pH adjusted to 8 to 10. The invention further provides permanent waving compositions comprising as main ingredients cysteine and N-carbamoylcysteine in a combined concentration of 3 to 20% by weight and in the form of an aqueous solution having a pH adjusted to 8 to 10.

These permanent waving compositions are not only suitable for waving the hair but also usable for straightening naturally or artificially curled hair.

DETAILED DESCRIPTION OF THE INVENTION

We have carried out intensive research in an attempt to provide permanent waving compositions which act mildly on the human hair and skin and have no unpleasant odor but high stability during storage and application, and found that this object can be fulfilled by the use of N-carbamoylcysteine as a main ingredient. It was totally unknown to use N-carbamoylcysteine as the main ingredient of permanent waving compositions. Our continued research has further revealed that the use of cysteine and N-carbamoylcysteine in admixture also affords similarly outstanding permanent waving compositions.

Stated more specifically, the permanent waving compositions of this invention are characterized in that the compositions comprise N-carbamoylcysteine. Typical of the present waving compositions are those containing 3 to 20% by weight of N-carbamoylcysteine as the single main ingredient and in the form of an aqueous solution having an adjusted pH of 8 to 10.

The N-carbamoylcysteine to be used in this invention is preferably N-carbamoyl-L-cysteine or N-carbamoyl-DL-cysteine from the viewpoint of practical usefulness but can be N-carbamoyl-D-cysteine. N-carbamoyl-L-cysteine can be prepared easily, for example, by reacting L-cysteine with potassium cyanate. Since it is possible to synthesize N-carbamoyl-DL-cysteine from an inexpensive industrial material, the compound can presumably be prepared more economically than N-carbamoyl-L-cysteine. We have found that N-carbamoyl-L-cysteine and N-carbamoyl-DL-cysteine are both extremely low in toxicity. The $LD_{50}$ values of these compounds as determined on mice by oral administration are 13.5 g/kg for N-carbamoyl-L-cysteine and 13.1 g/kg for N-carbamoyl-DL-cysteine.

The permanent waving compositions comprising N-carbamoylcysteine as the main ingredient contain this compound in a concentration of 3 to 20% by weight according to the present invention. For use as cold-waving preparations at room temperature, the present waving compositions preferably contain 5 to 10% by weight of the compound, while compositions of lower concentrations are usable for waving at elevated temperatures.

The N-carbamoylcysteine, whether of the L-form or D-form or DL-form, makes no difference in the effect achieved insofar as it is used in an equal concentration.

While the permanent waving compositions comprising N-carbamoylcysteine as the single main ingredient are typical of the present invention, other important embodiments thereof are waving compositions containing both cysteine and N-carbamoylcysteine as main ingredients. Where specifically stated, permanent waving compositions exhibit a moderate action, are free from any unpleasant odor and have high stability when in the form of an aqueous solution comprising both cysteine and N-carbamoylcysteine, containing the N-carbamoylcysteine in a greater proportion than the cysteine to N-carbamoylcysteine molar ratio of 90:10 and having a pH adjusted to 8 to 10. The compositions contain both cysteine and N-carbamoylcysteine in a combined concentration of 3 to 20% by weight.

The waving compositions must contain N-carbamoylcysteine in a greater proportion than the cysteine to N-carbamoylcysteine molar ratio of 90:10. With a smaller amount of N-carbamoylcysteine present, the composition will have insufficient stability during application or storage. With an increase in the proportion of N-carbamoylcysteine, the composition has higher stability but tends to produce a somewhat reduced waving effect. Further since N-carbamoylcysteine has about 1.35 times the molecular weight of cysteine, the combined amount of cysteine and N-carbamoylcysteine needed for achieving a given waving effect increases with the increase in the proportion of N-carbamoylcysteine. Thus it is not always economically desirable to use a larger proportion of N-carbamoylcysteine. Preferably, therefore, the permanent waving compositions should have a cysteine to N-carbamoylcysteine molar ratio in the range of 90:10 to 50:50 so as to be acceptable in respect of waving effect, stability and economy. If the stability during storage as well as during application is especially important, compositions with a cysteine to N-carbamoylcysteine molar ratio of 70:30 to 50:50 are more preferable. Such compositions are exceedingly useful. Even when the above molar ratio ranges from 90:10 to 70:30, the composition is usable with good results if stored or applied with care. In fact, the composition is much superior to those containing cysteine alone.

The cysteine to be used conjointly with N-carbamoylcysteine may be of the L-form, D-from or DL-form. Similarly the N-carbamoylcysteine may be of the L-form, D-form or DL-form. The combined amount of cysteine and N-carbamoylcysteine contained in the waving compositions is usually 3 to 20% by weight. For use as cold-waving preparations at room temperature, the waving compositions preferably contain these ingredients in a combined concentration of 5 to 10% by weight. The compositions are usable at lower concentrations for waving at elevated temperatures.

The permanent waving compositions of this invention are in the form of an aqueous solution having its pH adjusted to 8 to 10, preferably 8.7 to 9.5. At a pH of below 8.7, N-carbamoylcysteine is not easily soluble, whereas pH values in excess of 9.5 are not needed for usual applications. The pH is adjustable with various inorganic bases or organic bases. Examples of useful inorganic bases are ammonia, sodium hydroxide, potassium hydroxide, etc. Examples of suitable organic bases are monoethanolamine, triethanolamine and other amines. Among these bases, monoethanolamine is especially preferable to use.

In addition to the foregoing main ingredient or ingredients and pH adjusting agent, penetrating agents, metal chelating agents and other additives can be incorporated into the permanent waving compositions of this invention to improve the effect of the compositions. The penetrating agent permits the main ingredient to penetrate into the hair more effectively to afford a stabilized effect of permanent waving. Examples of useful penetrating agents are polyoxyethylene and higher alcohol ethers or higher fatty acid esters thereof. Other surfactants are also usable. These penetrating agents are used usually in a concentration of about 0.1 to about 1% by weight. The metal chelating agent is effective in imparting enhanced stability to the main ingredient and also in giving an attractive finish to the hair. Examples of useful metal chelating agents are ethylenediaminetetraacetic acid (EDTA) and water-soluble salts thereof, which are used in a concentration of 0.01 to 0.1% by weight. Other additives such as antiseptics, wetting agents and thickeners, perfumes, coloring agents, etc. can be incorporated into the present compositions when so desired.

The permanent waving compositions of this invention are applied to the hair by the cold-waving process, elevated temperatures waving process, or ironing process used for the male hair. These processes are well-known in detail to one skilled in the art. When waving the hair by the cold process, the composition of this invention is fully applied to the hair as held in the desired form to plasticize the hair. The hair is thereafter subjected to an oxidizing condition and thereby set to the form in a known manner as by being exposed to air for a prolonged period of time or by being brought into contact with an aqueous solution of inorganic oxidizing agent for a short period of time. Examples of useful inorganic oxidizing agents are alkali metal salts of bromic acid, hydrogen peroxide, etc.

The permanent waving compositions of this invention are usable for waving the hair and also for uncurling naturally or artificially waved hair. In the latter case, the composition is applied to the hair, which is thereafter straightened and then set to the straight form.

The permanent waving compositions of the present invention have the following advantages.

(1) The mild action on the hair is unlikely to break or remove the hair and cause damage to the hair, permitting the waved hair to retain natural softness and sheen.

(2) The moderate action on the skin will not cause any rash or damage to the scalp. When comprising N-carbamoylcysteine alone or both cysteine and N-carbamoylcysteine with the latter proportion in excess of the cysteine to N-carbamoylcysteine molar ratio of 70:30, the waving compositions of this invention can be used repeatedly without causing the trouble such as white powder bonded to the hands of the hair-dressers.

(3) The compositions are free from the unpleasant odor attributable to the presence of thioglycolic acid and are therefore very agreeable to use.

(4) The compositions which contain N-carbamoylcysteine alone or which contain both cysteine and N-carbamoylcysteine with the proportion of the latter in excess of the cysteine to N-carbamoylcysteine molar ratio of 70:30 are usable without involving the separation of white powder that would lead to a reduced work efficiency or without permitting the deposition of white powder on the hair that would impair the appearance of the finished hair.

(5) While in storage, the present compositions retain the reducing ability at a higher level than the waving compositions containing cysteine as the single main ingredient. The waving compositions of the invention which contain N-carbamoylcysteine alone or which contain both cysteine and N-carbamoylcysteine with the latter proportion in excess of the cysteine to N-carbamoylcysteine molar ratio of 70:30, even when oxidized in the ambience, will not deposit white powder which is hardly soluble in water.

The description given above will indicate that the permanent waving compositions of the present invention are very desirable for professional and home uses.

The invention will be described below in greater detail with reference to examples, which are in no way limitative.

EXAMPLE 1

Six kinds of cold-waving solutions were prepared as listed in Table 1 below. Of these solutions, Solutions A, B, C and D are examples of the invention, while Solutions E and F are reference examples for comparison.

TABLE 1

| | Solution | | | | | |
|---|---|---|---|---|---|---|
| | Example | | | | Ref. example | |
| Ingredient | A | B | C | D | E | F |
| N-Carbamoyl-L-cysteine (g) | 8.0 | — | 5.5 | — | — | — |
| (mole) | 0.049 | | 0.034 | | | |
| N-Carbamoyl-DL-cysteine(g) | — | 8.0 | — | 5.5 | — | — |
| (mole) | | 0.049 | | 0.034 | | |
| L-Cysteine (g) | — | — | — | — | 6.0 | 4.0 |
| (mole) | | | | | 0.050 | 0.033 |
| Monoethanolamine (ml) | 4.2 | 4.2 | 3.0 | 3.0 | 3.4 | 2.4 |
| Tetrasodium EDTA (g) | 0.05 | 0.05 | 0.05 | 0.05 | 0.05 | 0.05 |
| Polyoxyethylene (20) oleyl ether (g) | 0.5 | 0.5 | 0.5 | 0.5 | 0.5 | 0.5 |
| Total volume (ml) | 100 | 100 | 100 | 100 | 100 | 100 |
| pH (26° C.) | 9.1 | 9.1 | 9.1 | 9.1 | 9.1 | 9.1 |

For the preparation of each cold-waving solution, monoethanolamine, N-carbamoylcysteine or L-cysteine, tetrasodium ethylenediaminetetraacetate (tetrasodium EDTA) and polyoxyethylene (20) oleyl ether were added to purified water with stirring in the order mentioned, and the solution was adjusted to 100 ml while adjusting the pH of thereof to 9.1 with monoethanolamine. The quantity of monoethanolamine listed in Table 1 is the combined quantity of the portion of the amine initially added and the portion used for pH adjustment.

The cold-waving solution listed in Table 1 was applied to tresses of washed hair, which were then wound on curlers, further wetted with the solution and thereafter allowed to stand for 15 minutes. Subsequently the tresses were rinsed with water to remove the waving solution. The tresses were set with a 5% potassium bromate solution, rinsed with water, dried and released from the curlers. The same procedure as above was repeated with use of all the solutions given in Table 1.

Solutions A, B and E produced very satisfactory waves, while Solutions C, D and F resulted in waves of somewhat reduced tightness which nevertheless were found fully satisfactory.

EXAMPLE 2

The six kinds of cold-waving solutions prepared in Example 1 were tested for storage stability.

A 100-ml portion of each of the solutions shown in Table 1 was placed into a 200-ml colorless wide-mouthed reagent bottle and allowed to stand for four weeks at room temperature (20° to 25° C.) with the mouth of the bottle left open.

Every week after the start of the testing, a 5.0-ml portion of the solution was withdrawn from the bottle, and the reducing substance therein was determined with use of iodine by the following method. The 5.0-ml portion of the solution collected was diluted with purified water to 50 ml, and the diluted solution was used as a test solution. A 25.0-ml quantity of 0.1 N iodine solution was placed into a 200-ml Erlenmeyer flask equipped with a ground stopper and containing 50 ml of purified water and 5.0 ml of 30% sulfuric acid. A 20.0-ml portion of the test solution was further placed into the flask, which was then sealed off and shaken. The resulting mixture was thereafter allowed to stand at room temperature for 15 minutes and subsequently titrated with a 0.1 N standard solution of sodium thiosulfate. The amount of the standard solution consumed was measured. Separately a blank test was conducted to determine the amount of 0.1 N sodium thiosulfate standard solution consumed. The difference between the consumed amounts of the standard solution was taken as a characteristic value indicative of the content of the reducing substance in the sampled solution. To indicate the ability of the solution to retain the reducing substance, namely the retention of the substance, the characteristic values thus determined at an interval of one week were expressed in percentage relative to the corresponding characteristic value of the cold-waving solution as determined immediately after preparation and calculated as 100%. Table 2 shows the results.

TABLE 2

| Cold-waving solution | Retention of reducing substance (%) | | | |
|---|---|---|---|---|
| | In 1 week | In 2 weeks | In 3 weeks | In 4 weeks |
| Example A | 95.0 | 90.5 | 87.0 | 81.0 |
| B | 93.0 | 89.5 | 86.5 | 80.0 |
| C | 93.5 | 88.0 | 84.0 | 77.0 |
| D | 93.0 | 87.5 | 82.5 | 76.5 |
| Ref. Ex. E | 95.5 | 90.0 | 78.0 | 74.5 |
| F | 92.0 | 85.0 | 71.5 | 60.0 |

Table 2 reveals that the cold-waving solutions comprising N-carbamoylcysteine retain the reducing ability at a higher level than those containing L-cysteine.

It was further found that white powder of cystine separated out from Solution E on the 8th day and from Solution F on the 10th day, these solutions containing L-cysteine, whereas none of Solutions A, B, C and D containing N-carbamoylcysteine yielded white powder on lapse of 4 weeks.

EXAMPLE 3

Eleven kinds of test solutions were prepared with use of L-cysteine and N-carbamoylcysteine in varying ratios as shown in Table 3 to test the solutions for storage stability. Basically these solutions have the following composition.

| L-Cysteine, or L-cysteine and N-carbamoyl-L-cysteine | 0.05 mole |
|---|---|
| Monoethanolamine | 3.4 to 3.8 ml |
| Tetrasodium ethylenediaminetetraacetate | 0.05 g |
| Total volume | 100 ml |
| pH (26° C.) | 9.1 |

Table 3 also shows the quantities of L-cysteine, N-carbamoyl-L-cysteine and monoethanolamine used for the test solutions. Each of the solutions was prepared by adding monoethanolamine (about 3 ml), L-cysteine, N-carbamoyl-L-cysteine and tetrasodium ethylenediaminetetraacetate to about 80 ml of purified water in the order mentioned with stirring, and adjusting the resulting solution to 100 ml with its pH adjusted to 9.1 with monoethanolamine. Table 3 shows the combined quantity of monoethanolamine used for the solution. Test Solution A is a reference example.

between Tables 3 and 4 reveals that N-carbamoylcysteine is exceedingly superior.

TABLE 3

| Test solution | L-Cysteine (A) (g) | (mole) | N-Carbamoyl-L-cysteine (B) (g) | (mole) | A/B mole ratio | Mono-ethanol-amine (ml) | Days elapsed before deposition of white powder |
|---|---|---|---|---|---|---|---|
| Ref. Ex. | | | | | | | |
| A | 6.1 | 0.050 | 0 | 0 | 100:0 | 3.4 | 9 Days |
| Example | | | | | | | |
| B | 5.5 | 0.045 | 0.82 | 0.005 | 90:10 | 3.5 | 15 Days |
| C | 4.8 | 0.040 | 1.6 | 0.010 | 80:20 | 3.6 | 32 Days |
| D | 4.2 | 0.035 | 2.5 | 0.015 | 70:30 | 3.6 | Over 60 Days |
| E | 3.6 | 0.030 | 3.3 | 0.020 | 60:40 | 3.7 | " |
| F | 3.0 | 0.025 | 4.1 | 0.025 | 50:50 | 3.8 | " |
| G | 2.4 | 0.020 | 4.9 | 0.030 | 40:60 | 3.9 | " |
| H | 1.8 | 0.015 | 5.8 | 0.035 | 30:70 | 4.0 | " |
| I | 1.2 | 0.010 | 6.6 | 0.040 | 20:80 | 4.0 | " |
| J | 0.6 | 0.005 | 7.1 | 0.045 | 10:90 | 4.1 | " |
| K | 0 | 0 | 8.2 | 0.050 | 0:100 | 4.2 | " |

The test solutions were prepared on the same day, placed into 200-ml colorless wide-mouthed reagent bottles respectively and allowed to stand at room temperature (20° to 26° C.) for 60 days with the mouths of the bottles left open. Consequently white powder of cystine separated out on the 9th day from Test Solution A containing L-cysteine alone, whereas Test Solutions B and C further containing N-carbamoyl-L-cysteine yielded white powder on the 15th day and 32nd day respectively. No powdery deposition was found in Test Solutions D to K even after the lapse of 60 days. This indicates that the use of N-carbamoylcysteine conjointly with L-cysteine affords greatly improved storage stability.

For reference, the same experiment as above was conducted concurrently with the above experiment, except that N-acetyl-L-cysteine was used in place of N-carbamoyl-L-cysteine to compare N-carbamoylcysteine with N-acetylcysteine in respect of the stabilizing effect produced. Table 4 shows the quantities of L-cysteine, N-acetyl-L-cysteine and monoethanolamine used for the test solutions as well as the results of the experiment. The test solutions were prepared on the same day as Test Solutions A to K stated above and allowed to stand under exactly the same conditions. Test Solution L is equivalent to Test Solution A.

EXAMPLE 4

Cold-Waving Solutions A, B, C, D, E, F, G, I and K were prepared which corresponded to Test Solutions A, B, C, D, E, F, G, I and K listed in Table 3 in Example 3. These waving solutions had the same compositions as the above test solutions except that 0.5 g of polyoxyethylene (20) oleyl ether was added to 100 ml of each solution. The cold-waving solutions were tested for waving effect.

About 400 filaments of untreated human hair were bundled and fastened together with a thread at one end, then shampooed and dried to prepare a hair specimen having a uniform filament length of 25 cm. One of the cold-waving solution was applied to the specimen, which was then held to a curler 1 cm in diameter as wound thereon and allowed to stand at room temperature for 20 minutes. The specimen was thereafter rinsed with water to remove the waving solution, a 5% potassium bromate solution applied to the rinsed specimen, and the specimen allowed to stand for 15 minutes. The hair specimen was rinsed with water, lightly dewatered and removed from the curler.

Immediately after the above treatment, the specimen was held in suspension, and the length of the specimen (linear distance between opposite ends) was measured in a wet state. The specimen in this state was allowed to

TABLE 4

| | | | (comparison) | | | | |
|---|---|---|---|---|---|---|---|
| Test solution | L-Cysteine (A) (g) | (mole) | N-Acetyl-L-cysteine (B) (g) | (mole) | A/B mole ratio | Mono-ethanol-amine (ml) | Days elapsed before deposition of white powder |
| Ref. Ex. | | | | | | | |
| L | 6.1 | 0.050 | 0 | 0 | 100:0 | 3.4 | 9 Days |
| Example | | | | | | | |
| M | 5.5 | 0.045 | 0.76 | 0.005 | 90:10 | 3.6 | 10 Days |
| N | 4.8 | 0.040 | 1.5 | 0.010 | 80:20 | 3.8 | 13 Days |
| O | 4.2 | 0.035 | 2.3 | 0.015 | 70:30 | 4.0 | 24 Days |
| P | 3.6 | 0.030 | 3.0 | 0.020 | 60:40 | 4.2 | 32 Days |
| Q | 3.0 | 0.025 | 3.8 | 0.025 | 50:50 | 4.4 | Over 60 Days |
| R | 2.4 | 0.020 | 4.5 | 0.030 | 40:60 | 4.4 | " |
| S | 1.8 | 0.015 | 5.3 | 0.035 | 30:70 | 4.5 | " |
| T | 1.2 | 0.010 | 6.0 | 0.040 | 20:80 | 4.5 | " |
| U | 0.6 | 0.005 | 6.8 | 0.045 | 10:90 | 4.6 | " |
| V | 0 | 0 | 7.6 | 0.050 | 0:100 | 4.6 | " |

To be sure, N-acetylcysteine also adds to the stability of cysteine as shown in Table 4, whereas comparison stand indoors for 2 days, and the length of the spontaneously dried specimen was similarly measured.

In this way, the nine kinds of the cold-waving solutions were tested at the same time for waving effect. The waving effect was calculated from the following equation.

$$\text{Waving effect (\%)} = \frac{Lo - L}{Lo} \times 100$$

wherein Lo is the initial length of the hair (25 cm), and L is the length of the treated hair.

Table 5 shows the appearance of the treated hair and the waving effect of each solution (average of two measurements).

TABLE 5

| Waving Soln. | Cysteine mole ratio* | Waving effect (%) | | Appearance of treated hair |
|---|---|---|---|---|
| | | After treatment** | 2 Days later | |
| A | 100:0 | 22.3 | 11.4 | Slight deposition of white powder |
| B | 90:10 | 21.3 | 11.5 | Reduced sheen |
| C | 80:20 | 20.5 | 12.0 | Satisfactory sheen |
| D | 70:30 | 20.0 | 12.2 | " |
| E | 60:40 | 19.4 | 12.7 | " |
| F | 50:50 | 18.7 | 13.0 | " |
| G | 40:60 | 18.4 | 13.0 | " |
| I | 20:80 | 17.7 | 15.2 | " |
| K | 0:100 | 17.3 | 15.2 | " |

Note
*Mole ratio of L-cysteine to N-carbamoyl-L-cysteine
**Immediately after the treatment Solution A containing L-cysteine alone produced the best waving effect immediately after the treatment but resulted in the lowest waving effect in two days, thus exhibiting poor wave retaining ability. With Solutions B to K, the waving effect achieved immediately after the treatment is lower than that of Solution A and reduces with an increase in the proportion of N-carbamoyl-L-cysteine, whereas the waving effect obtained in two days is conversely higher and increases with the increase of the proportion of the N-carbamoyl-L-cysteine. Thus Solutions B to K have improved ability to retain the wave.

The hair treated with Solution A appeared somewhat whitish and unsightly owing to the deposition of cystine, while this drawback diminishes with the increase in the proportion of N-carbamoyl-L-cysteine. It was found that none of Solutions C to K involved such a phenomenon.

What we claim is:

1. In a permanent waving composition comprising an aqueous solution the improvement comprising including therein as the main ingredient, 3–20 percent by weight of N-carbamoylcysteine, said aqueous solution having a pH of 8–10.

2. A permanent waving composition as defined in claim 1, wherein the N-carbamoylcysteine is N-carbamoyl-L-cysteine or N-carbamoyl-DL-cysteine.

3. The permanent waving composition of claim 1 in which there is present 0.1 to 1 percent by weight of a penetrating agent and 0.01 to 0.1 percent by weight of a metal chelating agent.

4. In a permanent waving composition comprising an aqueous solution the improvement comprising including therein cysteine and N-carbamoylcysteine as main ingredients, the combined concentration of cysteine plus N-carbamoylcysteine being 3 to 20 percent by weight, the molar ratio of cysteine to N-carbamoylcysteine being up to 90:10 and the pH of said aqueous solution being 8–10.

5. A permanent waving composition as defined in claim 4, wherein cysteine and N-carbamoylcysteine are contained in a molar ratio of from 70:30 to 50:50.

6. A permanent waving composition as defined in claim 4 or claim 5, wherein N-carbamoylcysteine is N-carbamoyl-L-cysteine or N-carbamoyl-DL-cysteine.

7. The permanent waving composition of claim 4 in which there is present 0.1 to 1 percent by weight of penetrating agent and 0.01 to 0.1 percent by weight of a metal chelating agent.

* * * * *